United States Patent
Otero-Millan et al.

(10) Patent No.: US 11,602,273 B2
(45) Date of Patent: *Mar. 14, 2023

(54) SYSTEM AND METHOD FOR USING MICROSACCADE DYNAMICS TO MEASURE ATTENTIONAL RESPONSE TO A STIMULUS

(71) Applicant: Dignity Health, San Francisco, CA (US)

(72) Inventors: Jorge Otero-Millan, Phoenix, AZ (US); Stephen L. Macknik, Anthem, AZ (US); Susana Martinez-Conde, Anthem, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 664 days.

This patent is subject to a terminal disclaimer.

(21) Appl. No.: 15/858,437

(22) Filed: Dec. 29, 2017

(65) Prior Publication Data

US 2018/0116507 A1 May 3, 2018

Related U.S. Application Data

(63) Continuation of application No. 14/359,235, filed as application No. PCT/US2012/066462 on Nov. 23, 2012, now Pat. No. 9,854,966.

(Continued)

(51) Int. Cl.
*A61B 3/113* (2006.01)
*A61B 5/16* (2006.01)
(Continued)

(52) U.S. Cl.
CPC .............. *A61B 3/113* (2013.01); *A61B 5/163* (2017.08); *A61B 5/165* (2013.01); *A61B 5/18* (2013.01); *A61B 5/7246* (2013.01)

(58) Field of Classification Search
CPC A61B 3/113; A61B 5/16; A61B 5/162; A61B 5/163; A61B 5/165; A61B 5/168; A61B 5/18

See application file for complete search history.

(56) References Cited

U.S. PATENT DOCUMENTS 4,456,347 A 6/1984 Stahly
4,815,839 A 3/1989 Waldorf
(Continued)

OTHER PUBLICATIONS

Martinez-Conde et al; Windows on the Mind; Aug. 2007; Scientific American, p. 57-63. (Year: 2007).*

(Continued)

*Primary Examiner* — Devin B Henson
*Assistant Examiner* — H. Q. Nguyen
(74) *Attorney, Agent, or Firm* — Quarles & Brady LLP

(57) ABSTRACT

A system and method for determining a subject's attentional response to a stimulus. The method includes measuring microsaccadic eye movement dynamics of the subject, detecting whether a microsaccadic signature (a suppression in microsaccadic rate) is present in the measured microsaccadic eye movement relative to a time of the stimulus, and correlating the subject's attentional response to the stimulus based on the detection. The method further includes determining that the stimulus was sensed if the microsaccadic signature is present and determining that the stimulus was not sensed if the microsaccadic signature is absent.

16 Claims, 3 Drawing Sheets

Related U.S. Application Data

(60) Provisional application No. 61/562,576, filed on Nov. 22, 2011.

(51) Int. Cl.
*A61B 5/18* (2006.01)
*A61B 5/00* (2006.01)

(56) References Cited

U.S. PATENT DOCUMENTS

| | | | |
|---|---|---|---|
| 5,137,345 A | 8/1992 | Waldorf | |
| 5,382,989 A | 1/1995 | Uomori et al. | |
| 6,290,357 B1* | 9/2001 | Massengill | A61B 3/024 351/209 |
| 8,668,337 B2 | 3/2014 | Waldorf | |
| 9,101,312 B2 | 8/2015 | Waldorf | |
| 9,123,050 B2* | 9/2015 | Ryu | G06Q 30/0244 |
| 11,013,441 B2 | 5/2021 | Samadani | |
| 2005/0073136 A1 | 4/2005 | Larsson et al. | |
| 2005/0128434 A1 | 6/2005 | Ianchulev et al. | |
| 2005/0200808 A1 | 9/2005 | Wyatt | |
| 2007/0265507 A1 | 11/2007 | De Lemos | |
| 2007/0273832 A1* | 11/2007 | Weinblatt | A61B 3/113 351/210 |
| 2009/0198148 A1 | 8/2009 | Lonky | |
| 2010/0039617 A1 | 2/2010 | Martinez-Conde et al. | |
| 2010/0191156 A1 | 7/2010 | Sakamoto et al. | |
| 2010/0277693 A1 | 11/2010 | Martinez-Conde et al. | |
| 2011/0109879 A1 | 5/2011 | Palti-Wasserman et al. | |
| 2012/0182523 A1 | 7/2012 | Wyatt | |
| 2012/0238903 A1 | 9/2012 | Martinez-Conde et al. | |

OTHER PUBLICATIONS

Ziad M. Hafed et al., Microsaccades as an Overt Measure of Covert Attention Shifts, Vision Research 42 (2002), pp. 2533-2545.

Engbert, R. et al. "Microsaccades uncover the orientation of covert attention." Vision research 43.9 (2003): 1035-1045.

* cited by examiner

SYSTEM AND METHOD FOR USING MICROSACCADE DYNAMICS TO MEASURE ATTENTIONAL RESPONSE TO A STIMULUS

CROSS REFERENCE TO RELATED APPLICATIONS

This application is a continuation of U.S. patent application Ser. No. 14/359,235 filed May 19, 2014, which represents the national stage entry of PCT International Application No. PCT/US2012/066462 filed Nov. 23, 2012, which claims the benefit of U.S. Provisional Patent Application Ser. No. 61/562,576 filed on Nov. 22, 2011, the disclosures of which are incorporated herein by reference in their entirety for all purposes.

BACKGROUND OF THE INVENTION

The present application is directed to monitoring eye movements to determine a subject's attentional response to a stimulus. In particular, the present application is directed to analyzing microsaccade dynamics for an exhibited microsaccadic signature to determine whether a subject senses a stimulus.

Little is known about the neuroscience of emotional manipulation with respect to cognition and attention. More specifically, there are currently no objective measures to determine how emotions are manipulated by narrative elements, such as rhetoric, media events, propaganda, unfolding events on the battlefield, or how narrative elements actually influence observers. Therefore, it would be desirable to provide a method and system for objectively measuring a subject's response to a stimulus, such as a narrative that invokes an emotional threat.

SUMMARY OF THE INVENTION

The present invention provides a method for determining a subject's attentional response to a stimulus. The method includes measuring microsaccadic eye movement dynamics of the subject, detecting whether a microsaccadic signature is present in the measured microsaccadic eye movement relative to a time of the stimulus, and correlating the subject's attentional response to the stimulus based on the detection. The method can further include determining that the stimulus was sensed if the microsaccadic signature is present and determining that the stimulus was not sensed if the microsaccadic signature is absent.

A system in accordance with the present invention includes an eye tracking device and a host operably connected to the eye tracking device. The eye tracking device is capable of detecting eye movement traces and the host is configured to receive the eye movement traces from the eye tracking device. The host is further configured to measure microsaccadic eye movement dynamics of the subject based on the eye movement traces, detect whether a microsaccadic signature is present in the measured microsaccadic eye movement relative to a time of the stimulus, and correlate the subject's attentional response to the stimulus based on the detection.

A method in accordance with the present invention includes determining a subject's attentional response to a stimulus. The method includes receiving eye movement traces of the subject over a time period including a time of the stimulus, determining, from the eye movement traces, a microsaccade rate of the subject over the time period, and detecting whether a microsaccadic signature is present in the eye movements relative to the time of the stimulus. The microsaccadic signature can be a suppression of the microsaccade rate below a baseline rate. The method can further include generating a report indicating the subject's attentional response to the stimulus based on the detection.

A method in accordance with the present invention includes determining a subject's attentional response to a stimulus. The method includes monitoring eye movements of the subject over a time period including a time of the stimulus, measuring microsaccadic eye movement dynamics of the subject based on the eye movements, and calculating, from the microsaccadic eye movement dynamics, microsaccade rate over a time period including a time of the stimulus. The method can further include detecting whether a microsaccade rate suppression event is present in the measured microsaccadic eye movement relative to the time of the stimulus, determining the subject's attentional response to the stimulus based on the detection, and generating a stimulus detection threshold based on the determined attentional response to the stimulus. The stimulus detection threshold can indicate a probability of the subject responding to the stimulus based on information about the stimulus.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
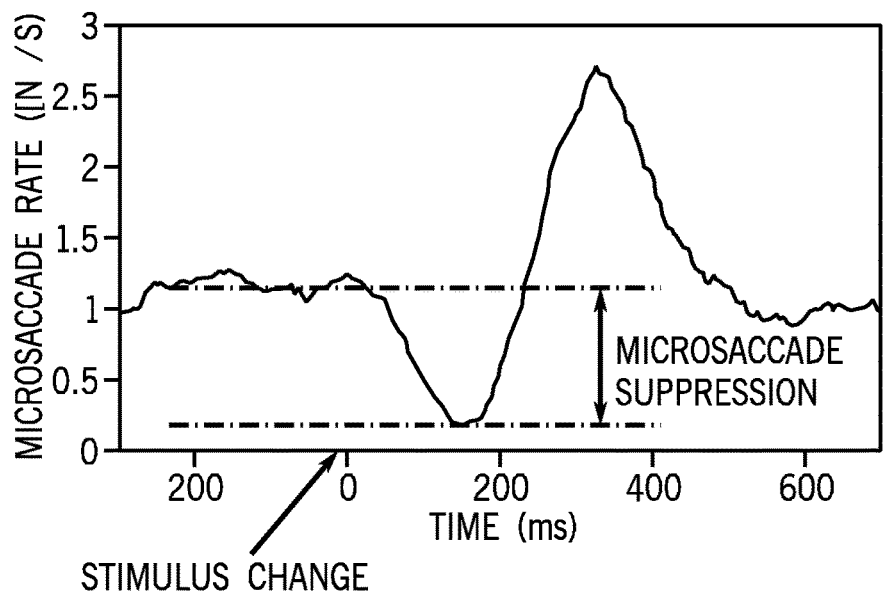
FIG. 1 is a graphical representation of microsaccade rate over time, illustrating an exhibited microsaccadic signature.

The present invention generally provides a method monitoring eye movements of a subject to determine the subject's attentional response to a stimulus. Such eye movements can include microsaccade dynamics, and more specifically, microsaccadic rate over a time period (including the time of stimulation). The microsaccadic rate can be analyzed to detect whether a microsaccadic signature was elicited within the time period. If no microsaccadic signature is observed, the stimulus was not sensed (that is, unconscious or no response). If the microsaccadic signature is observed, the stimulus was sensed and either a subconscious or conscious response may be concluded. Furthermore, if the microsaccadic signature is observed, properties of the microsaccadic signature can be analyzed to determine the magnitude of the response. This method can serve as an objective measurement of attentional response to a stimulus because, as further discussed below, microsaccades are involuntary movements that cannot be forced by the subject.

In a subject's visual field, visual attention may be focused according to the attentional spotlight. More specifically, the attentional spotlight can enhance perception at a given spatial focus within the visual field or can selectively enhance features of interest within the visual field. Furthermore, the attentional spotlight can suppress all areas outside the feature of interest. For example, when a human fixates their gaze, the eyes are only actually fixated 80% of the time, while saccades (quick, simultaneous movements of both eyes in the same direction) and microsaccades (involuntary saccades that occur during attempted fixation of the eyes, which are usually less than 1 degree in magnitude) occur the other 20% of the time. During this fixated gaze when the subject is attending covertly to a position away from the target of fixation, dual nodes of activity are generated in the superior colliculus (an area of the brain that targets both eye movements and attention). The first node of activity is at the center of the superior colliculus's visual map, which maintains fixation and targets fixational microsaccades. The second node of activity is in the periphery of the superior colliculus's map at the position of the attentional spotlight. When the superior colliculus is readout by brainstem mechanisms, the dual nodes activity are combined, resulting in microsaccades biased towards the location of the attentional spotlight. In other words, no matter where a subject fixates on an image, the rate and direction of microsaccades is influenced by the presence and position of the subject's target of interest on the image. The subject may overtly attend the interested target (by looking right at it) or covertly attend the target (by looking away from the target and secretly paying attention to the target). Even when covert attention is engaged, microsaccades are biased in a direction towards the attended region of interest in an involuntary and unconscious manner.

As described in U.S. Pat. No. 7,857,452, the entire contents of which are incorporated herein by reference, eye movements can be monitored to detect this bias. Generally, these detection methods include tracking a subject's eye position and detecting microsaccades from eye position traces. Example algorithms for detecting microsaccades objectively from eye position traces (e.g., from video, eye coil, optical, or other suitable tracking methods) include the Martinez-Conde and Macknik algorithm (Martinez-Conde S., Macknik S. L., Hubel D. H. (2000) Nature Neuroscience, incorporated herein by reference) and the Engbert algorithm (Engbert R., Kliegl R. (2003) Vision Res 4:1035-1045, incorporated herein by reference). Next, microsaccade position and direction can be determined and the subject's region of interest can be determined using this information. Several different methods can be used to make this determination. For example, one method includes determining trajectories of tracked microsaccades and extrapolating the trajectories within the subject's visual field to determine areas of trajectory intersection. A subject's region of interest is likely in regions where more intersections exist. Furthermore, the trajectories can be triangulated to determine the likely region of interest. Accordingly, because microsaccades are involuntary movements that are invisible to the subject who is making them, the subject's attentional focus (region of interest), whether covert or overt, can be objectively and non-invasively determined.

When the subject's attentional spotlight is activated, for example in response to a stimulus, the result is that microsaccades exhibit a stereotypical behavior—a "microsaccadic signature"—in which they are suppressed and then often rebound in rate. This is illustrated in FIG. 1, where at time t=0, microsaccadic rate drops significantly below a normal rate (that is, suppresses), rapidly increases above the normal rate (that is, rebounds), then returns back to the normal rate. A stimulus that activates the attentional spotlight can refer to any sensory stimulus (visual, auditory, olfactory, etc.), or cognitive process, that attracts attention of the subject to a target area in the subject's field of view. This can be as simple as an on/off-type stimulus, such as a flash of light, a flash of an image on a screen in the subject's field of view, an object appearing in the subject's field of view, etc. This can also refer to a target of interest in the subject's field of view that invokes an emotional response, for example in conjunction with narrative influence (such as a verbal emotionally charged threat or influential statement). In addition, the magnitude of the microsaccadic signature (for example, the magnitude of the suppression) may generally indicate the magnitude of the attentional spotlight. For example, the primary physiological effect of emotions is that they drive cognitive brain systems to focus spatial attention. Thus, invoking an emotional response can affect the location and magnitude of attentional spotlight, where a larger emotional response can invoke a larger suppression.

Figure 2:
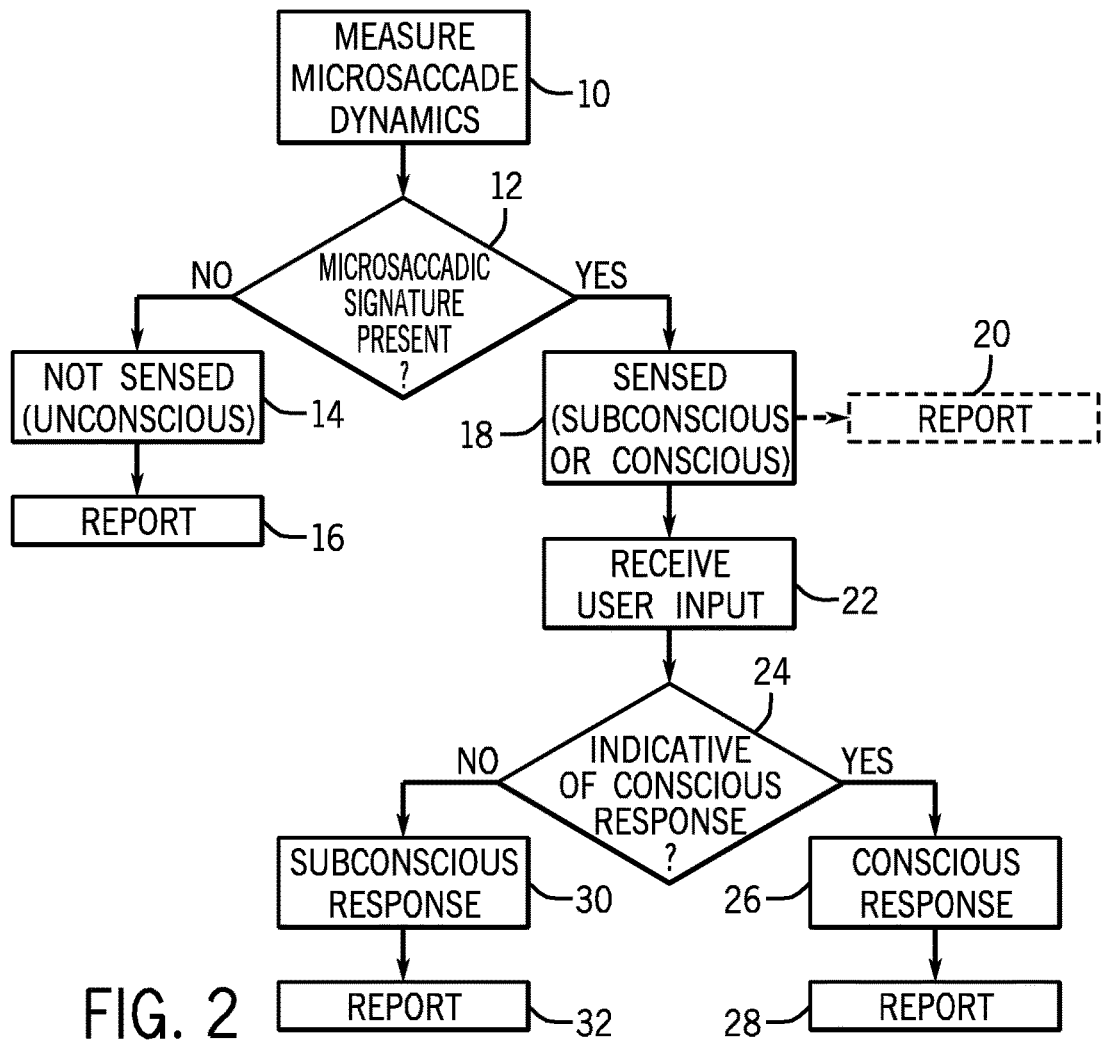
FIG. 2 is a flow chart setting forth the steps of a method for determining attentional response to a stimulus, in accordance with the present invention.
Figure 4:
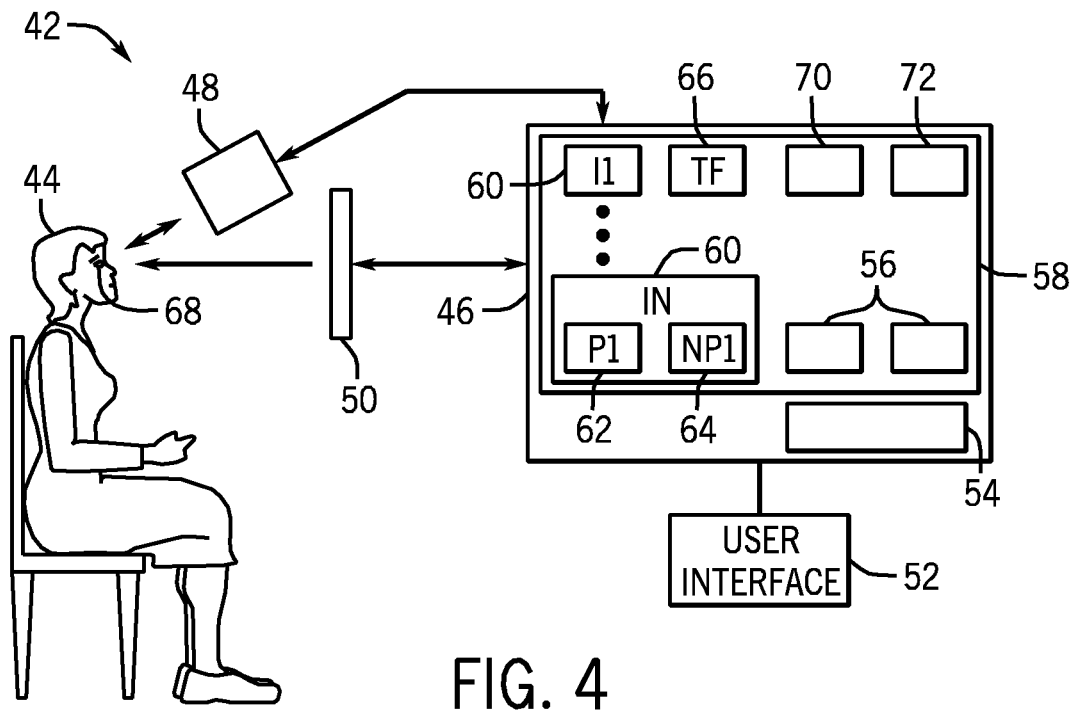
FIG. 4 is a schematic view of a system according to the present invention.
Figure 5:
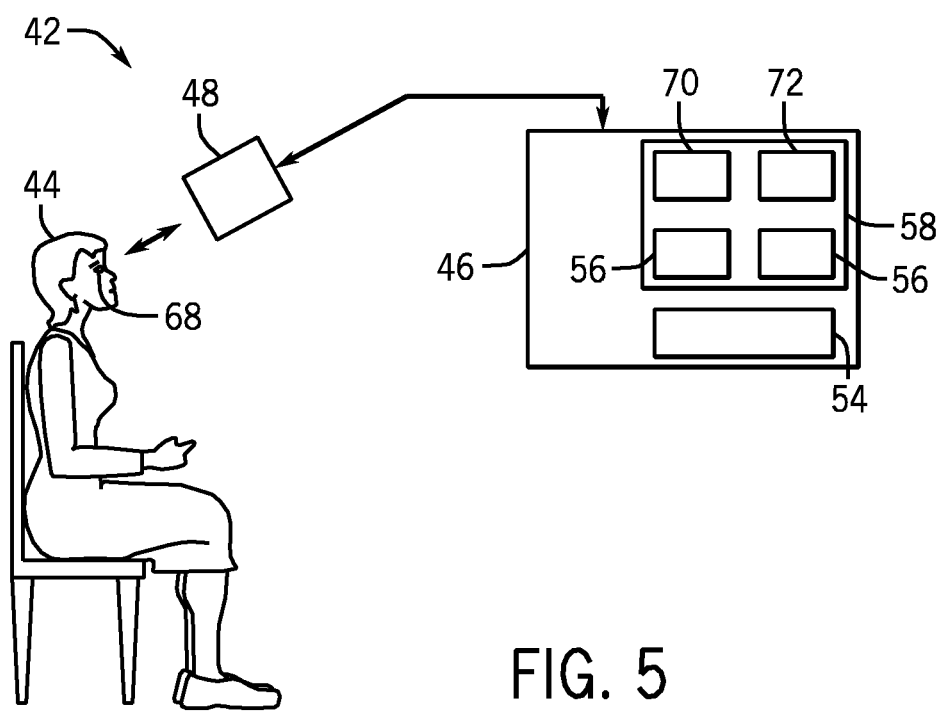
FIG. 5 is a schematic view of another system according to the present invention.

In light of the above, the present invention provides a method, as shown in FIG. 2, for objectively determining whether is stimulus is detected by a subject. The present invention further provides a system for carrying out this method, as illustrated in FIGS. 4 and 5 and further described below. Generally, the method can include measuring a subject's microsaccade dynamics over a time period and determining whether a stimulus presented within that time period was sensed or not sensed by the subject. More specifically, as shown in FIG. 2, a subject's microsaccade dynamics can be measured [process block 10]. Microsaccade dynamics can include microsaccade rate over a time period, for example wherein a stimulus is presented within that time period. These dynamics can be measured by monitoring eye movements and detecting microsaccades from eye position traces, as discussed above.

The microsaccade dynamics can then be analyzed to determine if a microsaccadic signature was present [process block 12]. This step can be performed by determining a baseline or normal microsaccade rate, and determining a relatively quick drop or suppression from the normal rate within the time period. On average, a human's normal microsaccade rate is about one microsaccade per second. For example, as shown in FIG. 1, the baseline microsaccade rate is relatively steady around one microsaccade per second, then at time t=0 (that is, time of stimulus), the microsaccade rate drops to almost zero (in less than 200 milliseconds), rebounds above the baseline rate, and returns back to the baseline rate. This entire microsaccadic signature occurs within about 500 milliseconds. In some applications, the microsaccadic signature can be determined by comparing the measured microsaccade rate to predetermined or stored thresholds.

If the microsaccadic signature is not detected, the stimulus was not sensed by the subject (in other words, the subject's brain was unconscious to the stimulus) [process block 14]. A report indicating this conclusion (that is, "not sensed" or "unconscious") can then be generated and displayed and/or recorded [process block 16]. If the microsaccadic signature is detected, the stimulus was sensed by the subject, either consciously or subconsciously [process block 18]. In some cases, a report indicating this conclusion (that is, "sensed") can then be generated and recorded and/or displayed [process block 20]. In addition, user input can be retrieved [process block 22]. This user input can include feedback from the user regarding whether they acknowledged a stimulus or not. Based on this user input, one can conclude whether the stimulus invoked a conscious response or a subconscious response [process block 24]. More specifically, if user input indicated the stimulus was detected, then the stimulus was consciously detected [process block 26]. A report indicating this conclusion (that is, "conscious response") can then be generated and displayed and/or recorded [process block 28]. If user input indicated the stimulus was not detected, then the stimulus was only subconsciously detected [process block 30]. A report indicating this conclusion (that is, "subconscious response") can then be generated and displayed and/or recorded [process block 32].

In some applications, generated reporting data from the above method, for example performed on one or more subjects, can then be used to provide general probabilities of a subject's attentional response to a given stimulus. For example, FIG. 3a graphically illustrates attentional response invoked by flashes of light (that is, stimuli) of various durations. Generally, at low durations, the luminance of the flash is too low for a subject's brain to detect; however, at long durations, the flash can be easily and consciously perceived. Accordingly, detection can improve as a function of stimulus duration. Thus, if the stimulus is a long flash of light (that is, long duration), the subject can detect it consciously and there will be a detectable microsaccadic signature, thereby illustrating a conscious response. A very short flash will result in neither conscious detection of the flash or an elicited microsaccadic signature, thereby illustrating that the brain is unconscious to the stimulus. A medium length flash will result in high probability of a microsaccadic signature, but lower probability of conscious detection. This can be referred to as a subconscious event because the brain "sees" the flash of light (otherwise, there would be no microsaccadic signature), but there was no conscious perception of the flash of light by the subject.

Figure 3A:
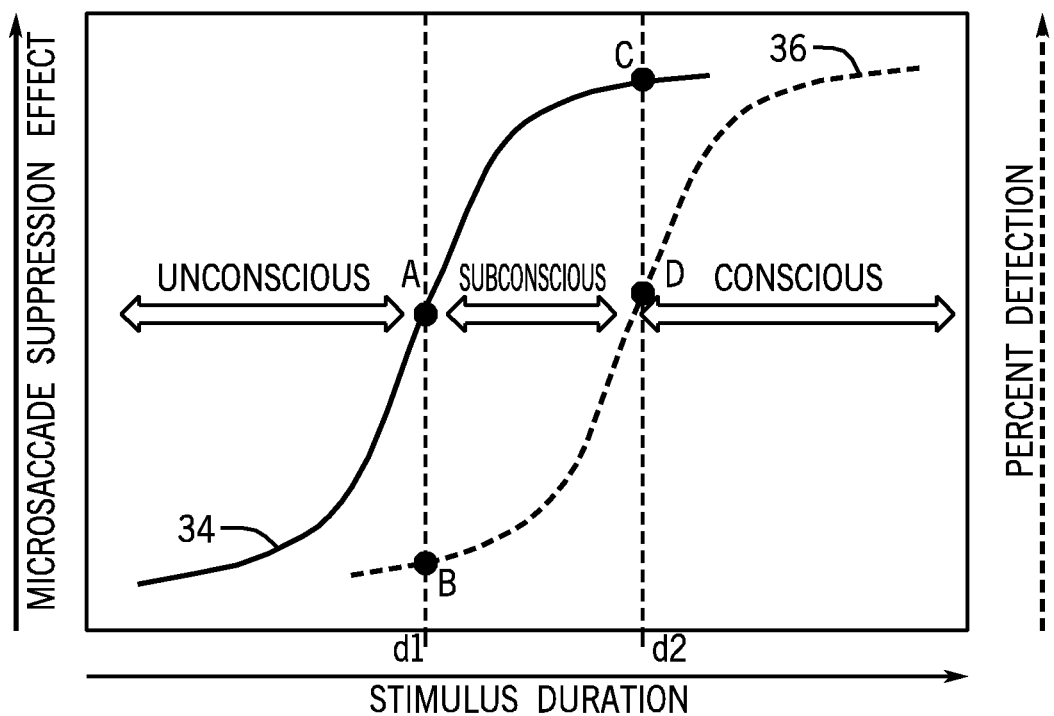
FIG. 3a is a graphical representation relating microsaccade suppression effect and percent conscious detection to duration of a stimulus.

More specifically, the x-axis of FIG. 3a illustrates relative stimulus duration (short to long). The y-axis illustrates two variables: probability of microsaccade suppression effect (low to high percent) and probability of conscious detection (low to high percent). Microsaccade suppression effect with respect to stimulus duration is illustrated by line 34, and percentage conscious detection with respect to stimulus duration is illustrated by line 36. Thus, generally, the area to the left of line 34 illustrates where the brain is unconscious to the stimulus (occurring at shorter stimulus durations), the area to the right of line 36 illustrates conscious detection of the stimulus (occurring at longer stimulus durations), and the area between lines 34 and 36 illustrates subconscious detection, where a microsaccadic signature is present, but conscious detection is not.

By way of example, at duration d1, there is about a 50% chance microsaccadic suppression will be invoked (point A), but a much smaller chance that conscious detection will occur (point B). At duration d2, there is a very high chance microsaccadic suppression with be invoked (point C), and about a 50% chance conscious detection will occur (point D). It is noted that microsaccadic suppression effect may coincide with conscious perception, but it can never be higher (or else the stimulus is unattended and therefore invisible perceptually). In other words, the chance of conscious detection cannot be higher than the chance of microsaccadic suppression. In addition, the lines 34 and 36 can be further refined based on additional generated data.

Figure 3B:
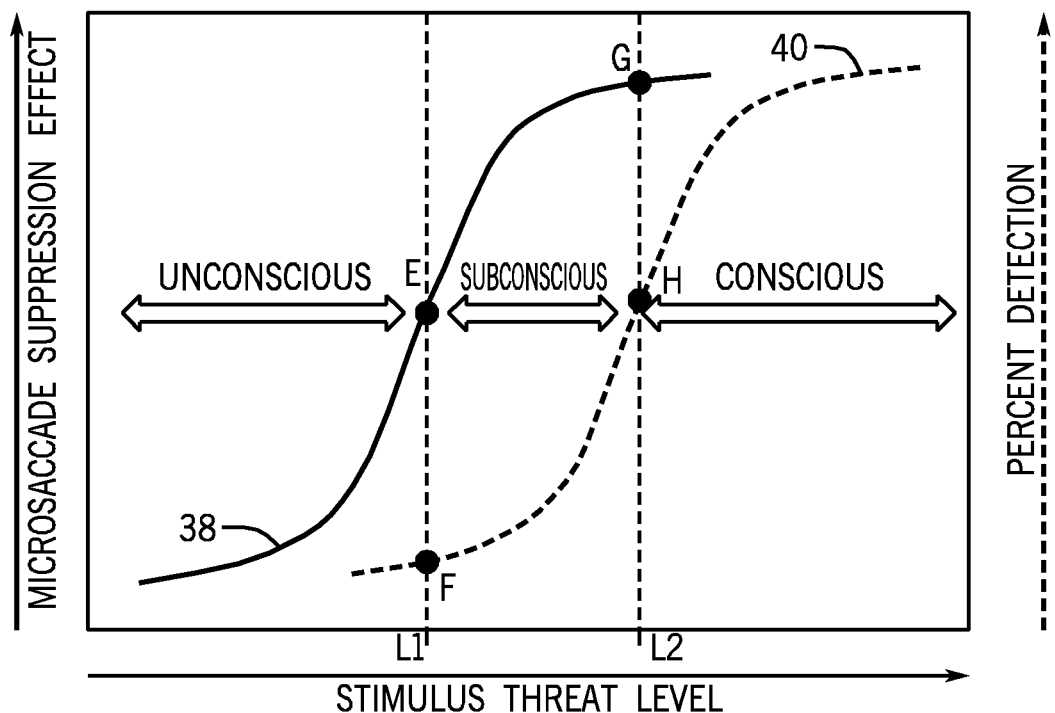
FIG. 3b is a graphical representation relating microsaccade suppression effect and percent conscious detection to threat level of a stimulus.

In another example, FIG. 3b graphically illustrates attentional response invoked by stimuli of various emotional threat levels. Generally, at low threat levels, a microsaccadic signature is not elicited, illustrating no emotional response. High threat levels, however, can evoke a microsaccade suppression and a conscious or visible emotional response. Thus, if the stimulus contains a high threat level, the subject will evoke a noticeable emotional response to the threat and there will be a detectable microsaccadic signature, illustrating a conscious event. A stimulus with low threat levels will result in neither emotional response or an elicited microsaccadic signature, indicating the brain is unconscious to a perceived threat. A "middle-grade" threat can result in high probability of a microsaccadic signature, but low probability of a conscious emotional response by the subject. Similar to that discussed above, this can be referred to as a subconscious event because the brain elicits an emotional response (otherwise, there would be no microsaccadic signature), but there was no conscious emotional response by the subject.

More specifically, the x-axis of FIG. 3b illustrates relative threat level (low to high). The y-axis illustrates two variables: probability of microsaccade suppression effect (low to high percent) and percentage of conscious detection (low to high percent). Microsaccadic suppression effect with respect to threat level is illustrated by line 38, and percentage conscious detection with respect to threat level is illustrated by line 40. Thus, the area to the left of line 38 illustrates unconscious, that is, no emotional response (occurring at low threat levels). The area to the right of line 40 illustrates conscious perception or a visible emotional response (occurring at high threat levels). The area between lines 38 and 40 illustrates subconscious detection, where a microsaccadic signature is present, but conscious perception is not. The lines 38 and 40 can be plotted and refined based data from one or more subjects tested at different threat levels, for example using the methods discussed above, thus providing general probabilities of a subject's attentional response at a given threat level.

By way of example, at a lower threat level L1, there is about a 50% chance microsaccadic suppression will be invoked (point E), but a much smaller chance that conscious response will occur (point F). At a higher threat level L2, there is a very high chance microsaccadic suppression with be invoked (point G), and about a 50% chance conscious response will occur (point H). In addition, the lines 38 and 40 can be further refined based on additional generated data. In some applications, stimuli of different threat levels can include emotional images where, for example an emotional image of a person exhibiting cheerful or happy body language would be at a very low threat level and an emotional image of a person exhibiting angry body language would be at a higher threat level.

In some applications, additional factors can be identified and analyzed in conjunction with the above-described method, such as other characteristics of microsaccade dynamics. In one example, the magnitude of the microsaccadic signature (for example, the magnitude of suppression from the normal rate) can be determined and can be correlated with a magnitude of the attentional response. With respect to the threat-level example discussed above, a higher magnitude of suppression can illustrate a larger threat level sensed or perceived. In another example, microsaccadic directions can also be identified. Then, by triangulating the bias in microsaccadic directions, and by determining the occurrence and magnitude of the microsaccadic signature, the location of the subject's locus of attention and its magnitude of attentional response can be identified with respect to a presented stimulus. In other words, using the method of the present invention, one can determine whether a stimulus was sensed, when it was sensed, and where in visual space the subject focuses upon sensing the stimulus.

Furthermore, in some applications, the method can further include predetermined probability thresholds (such as those discussed above with respect to FIG. 3a or 3b) to assess the reliability of the user input given. Generally, self-reporting may be unreliable due to unconscious and intentional criterion effects. However, the assessment of microsaccade dynamics can provide an unbiased and objective conclusion as to whether a stimulus was sensed or not (for example, a terrorist may lie, but his or her microsaccades cannot). Furthermore, with the aid of the predetermined probabilities, one can estimate whether a subject should have consciously perceived a stimulus at a given level, duration, etc. Even in the event that the microsaccadic signature is equal to conscious perception (for example, a visible reaction was observed), this method still has the advantage that it is unbiased and objective. In addition, such conclusions can be determined secretly and non-invasively, since eye movement and visible reactions can be observed from a standoff distance, as further discussed below.

Referring now to FIG. 4, a system 42 for detecting and analyzing eye movement of a subject to measure an attentional response of a subject 44 is presented. The system 42 can include a host 46 operably connected to an eye tracking device 48, a display 50, and a user interface 52. The host 46 can include one or more processors 54 operating under control of one or more computer programs 56 loaded from a non-transitory computer readable medium (memory) 58. As used herein, reference to a step performed by a computer program 56 is also a reference to the processor 54 that performed that step, for example in accordance with the process blocks discussed above. Example tracking devices 48 for use with the present invention can include the EyeLink II by SR Research (http://www.sr-research.com/fixed tech spec.php) or other equivalent eye tracking systems such as the IVIEW™ HI-SPEED 1250 tracking system by SensoMotoric Instruments (http://www.smivision.com/en/eye-gaze-tracking-systems/products/iview-x-hi-speed-.html).

The system 42 can operate by presenting a stimulus, such as an image, to the subject 44 through the display 50. For example, one of the processors 54, such as display processor, can retrieve one or more stored image files 60 from memory and present the images of a narrative to the subject on the display 16 either statically or dynamically. In this regard, the image files may each contain one or more static images or video sequences of images. In some cases, each of the image files 60 may include one or more emotive elements 62, 64 within the images that are intended to evoke a particular response along with the coordinate positions of the elements within each of the images. Where the images are presented dynamically, the processor 54 can maintain an image table 66 of image data including current positional information (such as x-y coordinates) for each of the elements as they are moved around the display 50. In some cases, the image files 60 also include related audio information. In such cases, the audio information can be presented to the subject 44 as part of a narrative along with the images through the display 50.

As the images are presented to the subject 44, the eye tracking device 48 can detect the position and movement of the subject's eyes 68. One of the processors 54, such as a tracking processor, can receive a position of the eyes 68, a distance between the subject 44 and the display 50 and calculate a center of the field of view of the eyes 68 on the display 50 under an appropriate coordinate system (such as x-y coordinates of the eye position on the display 50). Once calculated, the tracking processor 54 can receive the then-current image table 66 from the display processor 54, combine the data as a snapshot in time of eye position versus image data, and saves the data in a file 70. The measurement of microsaccade dynamics and analysis of microsaccade dynamics, such as determinations of microsaccadic signature or determinations of foci of attention, as described above with respect to FIG. 2, can be executed by one of the processors 54.

In addition, the subject 44 can provide user input through the user interface 52. For example, the subject 44 can press a button whenever a stimulus is acknowledged (whenever the subject sees an image). This user input can be analyzed in conjunction with time of stimulus and/or the determinations described above through one of the processors 54. Furthermore, reports, such as those described above with respect to FIG. 2, can be generated, stored, and/or displayed (via the display 50 or a different display). Accordingly, the system of FIG. 4 can be used to perform the method described above for detecting and analyzing eye movement of a subject to measure an attentional response of the subject 44. In some applications, the system of FIG. 4 can be used to generate reporting data for use in preparing probability charts and thresholds, as described above. Furthermore, in some applications, a processor 56 can analyze the generated reporting data to automatically prepare and/or refine the charts and thresholds. These charts and thresholds can then be stored in a file 72.

In one specific example, the system of FIG. 4 can be used as a flight simulator system. By monitoring a subject's eye movements with respect to images or videos presented to the subject, valuable data can be generated. For example, the system can detect when a subject notices a threat relative to when the threat is displayed to the subject.

In some applications, as shown in FIG. 5, another system 42 of the present invention can include an eye tracking device 48 and a host 46 with one or more processors 54 and memory 58 including one or more stored computer programs 56 and/or files 70, 72. The system 42 of FIG. 5 can be used to monitor eye movements to detect the presence or absence of microsaccadic signatures in response to outside stimuli (that is, stimuli not generated by the host 46). The system of FIG. 5 can also be used to monitor visible emotional responses to such stimuli (which may be used as user input), either through the video eye tracking device or a different form of eye tracking device (not shown). As a result, the system 42 of FIG. 5 can be used to monitor the subject from a standoff distance by using, for example, a telescopic lens with a video eye tracking system, for example without the subject's knowledge, to determine the subject's attentional response to a stimulus. For example, the subject's microsaccade dynamics can be measured and recorded within a time period including, for example, each time a microsaccadic signature was present and the time of occurrence. This recorded data can then be analyzed in conjunction with any visual emotional responses observed and/or knowledge of nearby events at the time of occurrence.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for determining a subject's attentional response to a stimulus, the method comprising the steps of:
receiving eye movement traces of the subject over a time period, wherein the stimulus is introduced after the time period has begun;
determining, from the eye movement traces, a microsaccade rate of the subject over the time period;
detecting whether a microsaccadic signature is present in the eye movements relative to the stimulus being introduced, the microsaccadic signature being a suppression of the microsaccade rate below a baseline rate; and
generating a report indicating the subject's attentional response to the stimulus based on the detection, wherein generating the report includes generating reporting data classifying the subject's attentional response to differentiate between one of an unconscious response, a conscious response, and a subconscious response.

2. The method of claim 1, wherein the baseline rate is a predetermined threshold obtained from a host device.

3. The method of claim 1 and further comprising receiving user input regarding whether the stimulus is acknowledged by the subject and correlating the subject's attentional response to the stimulus based on the detection and the user input.

4. The method of claim 1 and further comprising measuring a magnitude of the detected suppression as a difference between a suppressed rate during the detected suppression and the baseline rate and correlating the magnitude of the detected suppression to a relative magnitude of attentional response.

5. The method of claim 4, wherein generating the report includes indicating the relative magnitude of the subject's attentional response.

6. The method of claim 1 and further comprising determining, from the eye movement traces, trajectories of microsaccades with respect to a field of view of the subject.

7. The method of claim 6 and further comprising determining, from the eye movements, a directional bias of the microsaccades based on the trajectories and identifying a location of attentional focus of the subject with the field of view based on the directional bias.

8. The method of claim 7, wherein generating the report includes indicating the identified location of attentional focus of the subject.

9. The method of claim 1 and further comprising presenting the stimulus to the subject through one of an image and a video.

10. The method of claim 1, wherein receiving eye movement traces includes obtaining the eye movement traces from an eye tracking device.

11. The method of claim 10, wherein detecting whether the microsaccadic signature is present includes detecting, by a host device in communication with the eye tracking device, whether the microsaccadic signature is present.

12. The method of claim 1, wherein receiving eye movement traces includes obtaining recorded data of the eye movement traces.

13. The method of claim 1, wherein receiving eye movement traces includes obtaining the eye movement traces from one of an optical eye tracking device, an eye coil, and a video.

14. The method of claim 1 and further comprising generating a stimulus detection threshold, based on the detection, defining a probability of the subject responding to a future stimulus.

15. The method of claim 14, wherein the stimulus detection threshold includes a first stimulus detection threshold defining a probability of a subconscious response and a second stimulus detection threshold defining a probability of a conscious response.

16. The method of claim 1 and further comprising displaying the report on a display of a host device.

* * * * *